(12) United States Patent
Kong et al.

(10) Patent No.: US 7,677,249 B2
(45) Date of Patent: Mar. 16, 2010

(54) DEVICE AND METHOD FOR PROVIDING A LATERALIZATION EFFECT

(75) Inventors: James Kam Fu Kong, Hong Kong (CN); Eric Ping Chien, Hong Kong (CN); Keith Dip Kei Luk, Hong Kong (CN)

(73) Assignee: The University of Hong Kong, Hong Kong (CN)

( * ) Notice: Subject to any disclaimer, the term of this patent is extended or adjusted under 35 U.S.C. 154(b) by 1021 days.

(21) Appl. No.: 10/823,585

(22) Filed: Apr. 14, 2004

(65) Prior Publication Data
US 2004/0260299 A1    Dec. 23, 2004

Related U.S. Application Data

(60) Provisional application No. 60/463,186, filed on Apr. 16, 2003.

(51) Int. Cl.
| | |
|---|---|
| *A47B 7/00* | (2006.01) |
| *A61F 5/24* | (2006.01) |
| *A61F 5/28* | (2006.01) |
| *A61F 5/30* | (2006.01) |
| *A61F 5/34* | (2006.01) |
| *A61G 15/00* | (2006.01) |
| *A61F 5/37* | (2006.01) |
| *A61B 19/00* | (2006.01) |
| *A61F 5/00* | (2006.01) |

(52) U.S. Cl. .................. 128/845; 5/612; 128/95.1; 128/99.1; 128/112.1; 128/118.1; 128/846; 128/869; 128/870; 602/32; 602/33; 602/35; 602/36

(58) Field of Classification Search .............. 5/612; 128/845–846, 849, 95.1, 99.1, 112.1, 118.1, 128/869–870; 602/32–40; 606/86, 322; 269/322
See application file for complete search history.

(56) References Cited

U.S. PATENT DOCUMENTS

| 3,423,773 | A | * | 1/1969 | Yamate | 5/610 |
|---|---|---|---|---|---|
| 3,745,996 | A | * | 7/1973 | Rush, Sr. | 602/39 |
| 4,272,850 | A | | 6/1981 | Rule | |
| 4,641,641 | A | | 2/1987 | Strock | |
| 4,653,482 | A | * | 3/1987 | Kurland | 602/33 |
| 4,989,848 | A | * | 2/1991 | Monroe | 5/621 |
| 5,056,535 | A | * | 10/1991 | Bonnell | 128/882 |
| D347,103 | S | | 5/1994 | Berry | |
| 5,383,920 | A | | 1/1995 | Sikes | |
| 5,515,562 | A | | 5/1996 | Miller et al. | |

(Continued)

*Primary Examiner*—Patricia M Bianco
*Assistant Examiner*—Brandon Jackson
(74) *Attorney, Agent, or Firm*—Saliwanchik, Lloyd & Saliwanchik (57) ABSTRACT

The present invention relates generally to a device and method for providing a lateralization effect such as in a medical procedure. The lateralization device can have a supporting member, which can be adapted to be supported in a fixed position. A lateralization member can be provided to at least partially wrap around the supporting member and be mounted thereto to provide a lateralization effect. The lateralization member can be formed and/or adjusted to provide a variable lateralization. For example, the lateralization member can comprise a cylindrical member with an eccentric cut-out portion adapted to fit over the supporting member. The inter wall of the cut-out portion and the outer wall of the supporting member can be formed with interference fittings so that the lateralization member can rotate in relation to the supporting member to provide a variable lateralization.

13 Claims, 6 Drawing Sheets

U.S. PATENT DOCUMENTS

| | | | |
|---|---|---|---|
| 5,522,792 A * | 6/1996 | Bassett et al. | 602/19 |
| 5,623,949 A * | 4/1997 | Kostich | 128/845 |
| 5,658,315 A * | 8/1997 | Lamb et al. | 606/241 |
| 6,286,164 B1 * | 9/2001 | Lamb et al. | 5/600 |
| 6,295,671 B1 * | 10/2001 | Reesby et al. | 5/600 |
| 6,385,802 B1 * | 5/2002 | Roberts et al. | 5/621 |
| 6,467,487 B1 * | 10/2002 | Rios | 128/869 |
| 6,805,453 B2 * | 10/2004 | Spetzler et al. | 359/510 |
| 2007/0161935 A1 * | 7/2007 | Torrie et al. | 602/32 |

* cited by examiner

DEVICE AND METHOD FOR PROVIDING A LATERALIZATION EFFECT

CROSS REFERENCE TO RELATED APPLICATION

This patent application claims the benefit of U.S. Provisional Patent Application No. 60/463,186 filed Apr. 16, 2003.

FIELD OF THE INVENTION

The present invention relates generally to a device and method for providing a lateralization effect. In particular, the present invention relates to a device and method for providing an adequate lateralization vector force in a medical procedure.

BACKGROUND OF THE INVENTION

Hip arthroscopy is a common procedure for diagnosing and/or treating various hip conditions. Both supine and lateral approaches have been used in such a procedure. When performing such a procedure on a fracture table, complications can often occur, such as peroneal maceration and pudenal nerve palsy secondary to prolonged traction. U.S. Pat. No. 5,515,562 to Miller et al. discloses a perineal pad for a patient undergoing surgical procedures using manipulation or traction of the patient's lower extremities.

Devices for hip protection and stabilization are described, for example in U.S. Pat. No. 4,641,641 to Strock, as a protective appliance having an annular pad made of a resilient material. Adhesive strips are provided on one surface of the pad to secure the pad to the skin. The protective appliance also has a rigid dome-shaped shield carried in opposed pockets formed on the outer surface of the pad. Another known device for hip stabilization is disclosed in U.S. Pat. No. 5,383,920 to Sikes, which discloses a rigid outer shell and a cushioned pad on the inner surface of the shell. The cushioned pad is placed next to the joint area to be protected.

Body padding devices are also known. U.S. Pat. No. 4,272,850 to Rule discloses body protective pads that have an undersurface facing the body and a scored top surface in the pad to conform to the body area. In addition, U.S. Design Pat. No. 347,103 to Berry discloses another device for hip padding, which consists of a pad used externally to provide a cushioning effect to the hip region.

SUMMARY OF THE INVENTION

The present invention relates to a device and a method for providing and/or maintaining a lateralization effect. For example, the lateralization effect can be used to position the hip and the femur in a desired relationship during a hip arthroscopy. The lateralization device can comprise a supporting member, which can be adapted to be maintained in a fixed position. A lateralization member can provided and adapted to at least partially surround the supporting member and be mounted thereto. The lateralization member can be formed and/or adjusted to provide a lateralization effect, such as for the user's hip joint in a hip arthroscopy.

Optionally, the lateralization device can comprise a protection member surrounding the lateralization member. The protection member can be inflatable or gel-filled, or otherwise formed to provide a cushioning and/or protective effect for the user. The protection member can be removed and exchanged.

When using the lateralization device, the supporting member can be installed, such as on a support frame (e.g., a fracture table), to support the lateralization member. The lateralization member can be mounted onto the supporting member either before or after the supporting member is mounted in a fixed position. The lateralization member is capable of providing a lateralization effect. Additionally or alternatively, the lateralization member can be adapted to provide a variable lateralization effect.

According to another aspect, the present invention relates to a method for providing a desired lateralization effect, such as for the user's hip joint in a hip arthroscopy. The method can comprise providing a lateralization. Additionally or alternatively, the method can comprise varying the lateralization to reach a desired lateralization effect. The method can also comprise maintaining the desired lateralization effect.

BRIEF DESCRIPTION OF THE DRAWINGS

The detailed description of the present invention will be better understood in conjunction with the accompanying drawings which are for illustrative purposes only. The present invention is not limited to the embodiments shown in such drawings.

DESCRIPTION OF THE PREFERRED EMBODIMENTS

Exemplary lateralization devices and methods embodying the principles of the present invention are shown throughout the drawings. In the following description of various embodiments of the lateralization device, like reference numbers represent like elements or components and redundant description is omitted.

The present invention can provide a device and a method that is capable of providing an adequate lateralization effect. Additionally or alternative, the present invention can provide a device and a method capable of providing a variable lateralization effect. In one exemplary embodiment, the lateralization device 1 is capable of providing and/or maintaining a desirable lateralization and/or cushioning effect, such as for a patient's body portion in a medical procedure.

Figure 1:
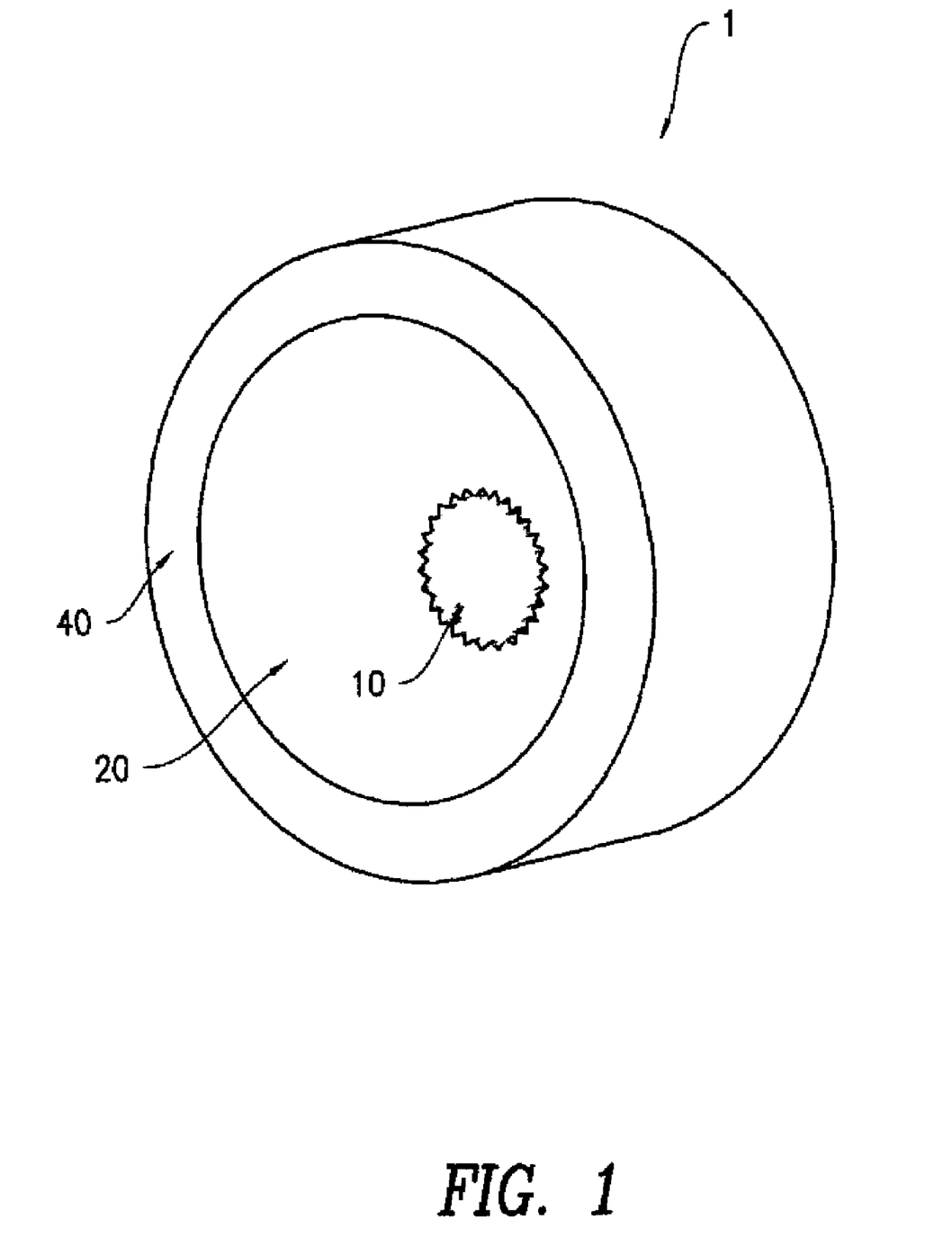
FIG. 1 illustrates a first embodiment of the lateralization device.

The lateralization device 1 can be formed in various manners. In one exemplary embodiment, such as shown in FIG. 1, the lateralization device 1 can comprise a supporting member 10, which can be adapted to be supported on a medical support frame, such as mounted on a fracture table 100 (see, FIGS. 4 to 6). A lateralization member 20 can be provided to be supported and mounted on the supporting member 10 as will be described in details below. The lateralization member 20 can be formed to be capable of providing a desired lateralization effect for the patient as will be described in greater details below.

The supporting member 10 of the lateralization device 1 can be formed in various manners to support and/or mount the lateralization member 20 on a support frame. For example, the supporting member 10 can comprise a post member 12 for engaging a complimentary structure on the lateralization member 20 as described below. In one exemplary embodiment, the supporting member 10 can comprise an extension portion 14 provided to fit in a corresponding cavity structure (not shown) in the support frame, such as a fracture table. In another exemplary embodiment, the supporting member 10 can be mounted onto the support frame in a fixed position. For example, the extension portion 14 can be fixed to the fracture table by conventional fasteners, such as knots, bolts, and the like, (not shown) to secure the lateralization device 1 on the fracture table. It will be appreciated that various alternative embodiments of mounting the supporting member 10 are still within the scope of the present invention.

Figure 2:
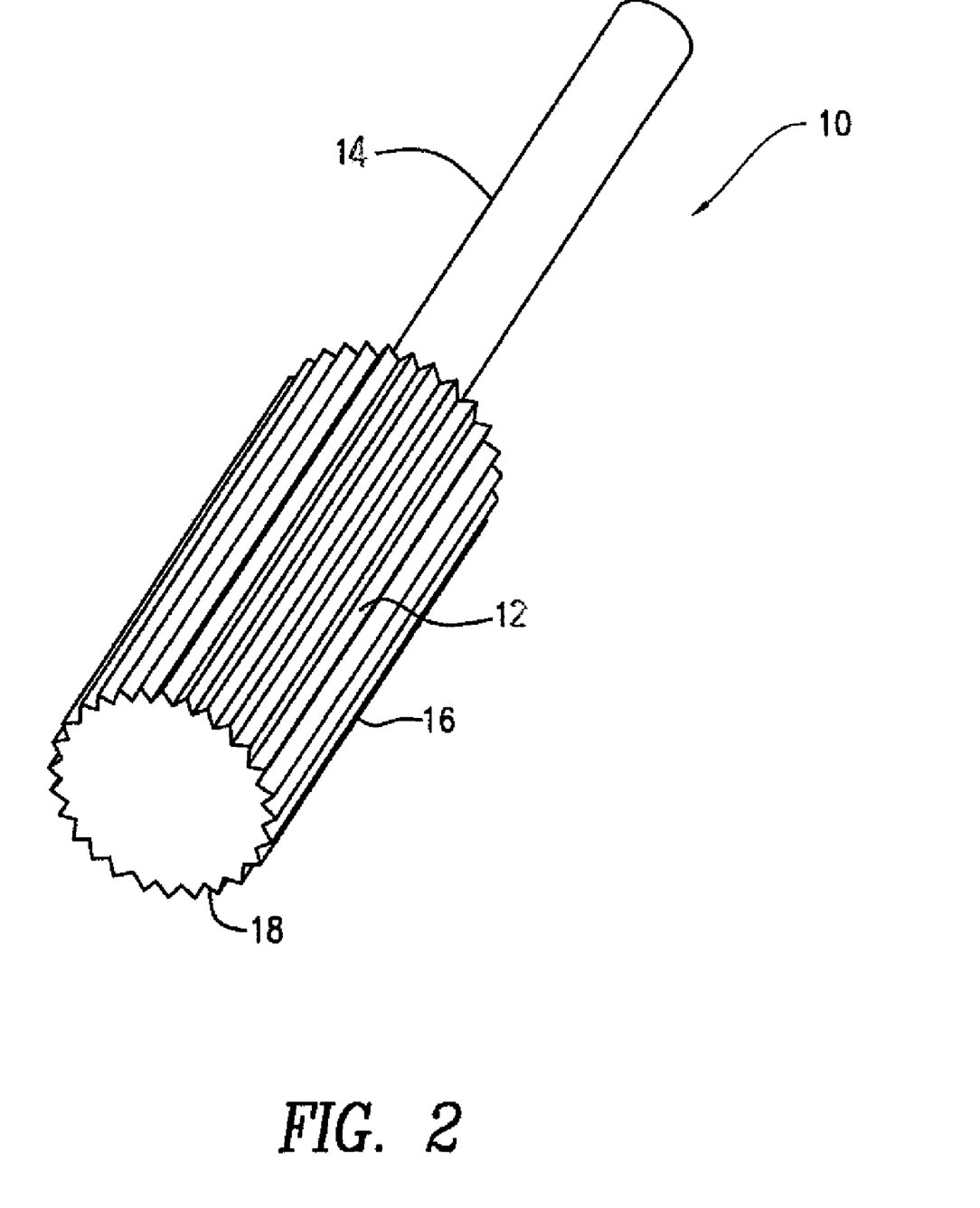
FIG. 2 illustrates the supporting member of the lateralization device-as shown in FIG. 1.

In one exemplary embodiment, the supporting member 10 can be formed in various manners to support the lateralization member 20 to provide a desired lateralization effect. For example, the supporting member 10 can be in the form of the post member 12 adapted to fit in a complimentary recessed portion formed on the lateralization member 20. In an exemplary embodiment, such as shown in FIG. 2, the supporting member 10 can be a substantially cylindrical member with various cross-sectional shapes. For example, the supporting member 10 can have a substantially circular, oval, or rectangular cross-sectional shape.

In another exemplary embodiment, the supporting member 10 can comprise a substantially circular outer wall 16 to be inserted in a circular cut-out portion in the lateralization member 20 as will be discussed below. In an exemplary embodiment, such as shown in FIG. 2, an interference fitting 18 can be formed on the outer wall 16 for engaging with a corresponding interference fitting 28 formed on the lateralization member 20 as will be discussed below. It will be appreciated that various alternative embodiments of the supporting member 10 and the post member 12 are still within the scope of the present invention.

The lateralization member 20 can be formed and/or adjusted in various manners to provide an adequate and/or desired lateralization effect for a user. In one exemplary embodiment, the lateralization member 20 can be formed with or adjusted to expand in a lateral direction to a sufficient lateral dimension. In an exemplary embodiment, the lateralization member 20 can maintain such dimension or expansion. In another exemplary embodiment, the lateralization member 20 can be formed to have sufficient lateral dimension. For example, the lateralization member 20 can be formed so that it is capable of moving the user's hip portion laterally outwardly to cause the hip joint to deflect from its normal position, thereby facilitating the hip arthroscopy. In a further exemplary embodiment, the lateralization member 20 can be made of various materials that can resist the pressure exerted thereon during a normal use without yielding.

In one exemplary embodiment, the lateralization member 20 can be formed in various shapes. In an exemplary embodiment, the lateralization member 20 can comprise a cylindrical member 22 with various cross-sectional shapes, such as circular, oval, or other curved shapes. For example, the lateralization member 20 can have a substantially circular cylindrical shape. In an exemplary embodiment, the cylindrical member 22 can have a smooth outer wall. It will be appreciated that various alternative embodiments of the cylindrical member 22 are still within the scope of the present invention.

Figure 3:
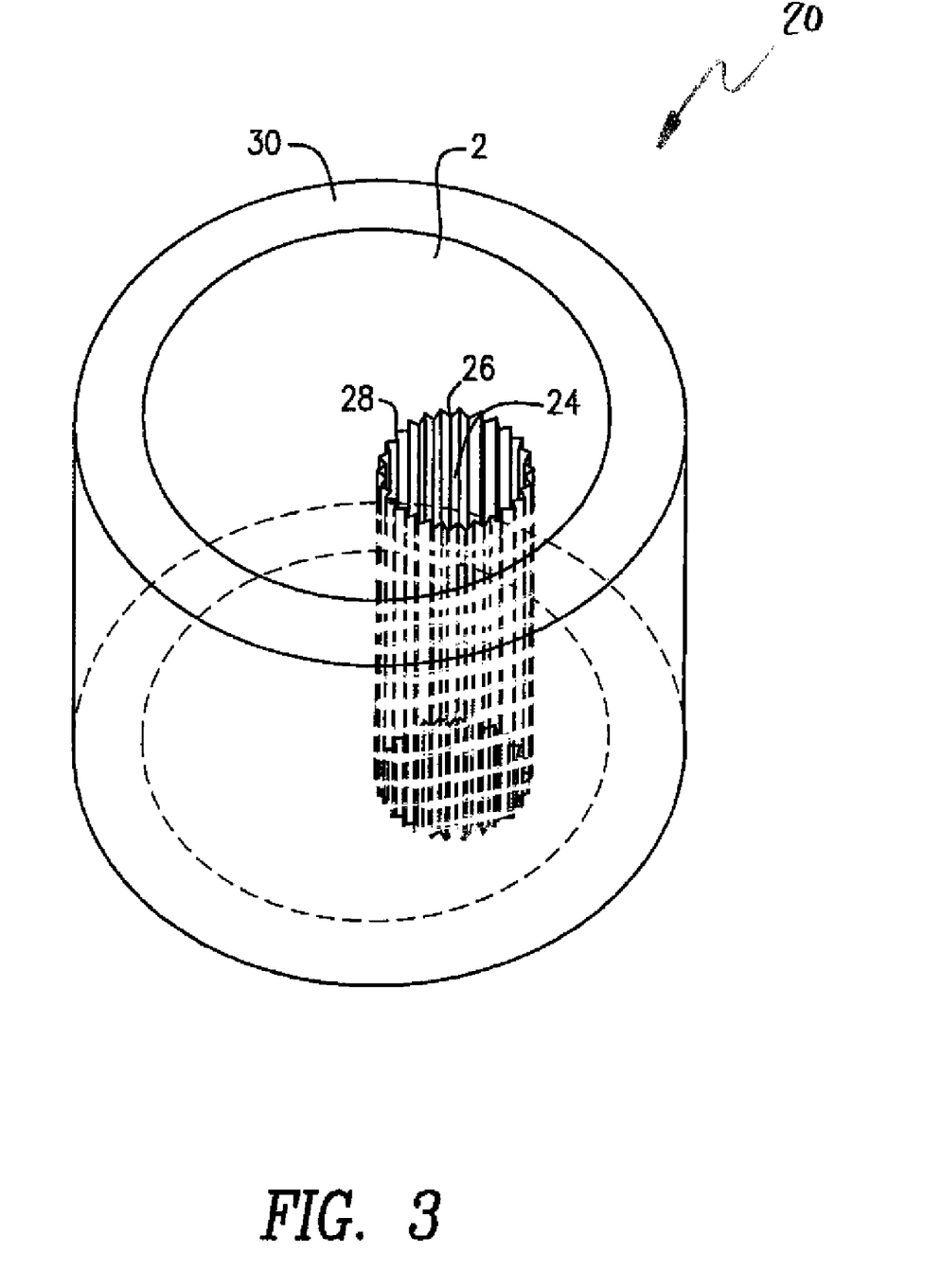
FIG. 3 illustrates the lateralization member of the lateralization device as shown in FIG. 1.

In one exemplary embodiment, the lateralization member 20 can have a recessed or cut-out portion 24 formed by an inner wall 26. The cut-out portion 24 can be adapted to fit over the supporting member 10 to be supported thereon. In an exemplary embodiment such as shown in FIG. 3, the cut-out portion 24 can extend longitudinally through the lateralization member 20. In another exemplary embodiment, the cut-out portion 24 can have a cylindrical shape with various cross-sectional shapes. For example, the cut-out portion 24 can be a substantially circular cylindrical opening, such as for fitting onto the circular post member 12. It will be appreciated that various alternative embodiments of the shape of the cut-out portion 24 are still within the scope of the present invention.

In another exemplary embodiment, the cut-out portion 24 can be located at various positions on the lateralization member 20. For example, the cut-out portion 24 can be positioned in the center of a circular cylindrical lateralization member 20 to provide a uniform lateralization. In one exemplary embodiment, the cut-out portion 24 can be formed in such a position on the lateralization member 20 so as to provide a variable lateralization. In an exemplary embodiment such as shown in FIG. 3, the cut-out portion 24 can be formed in an eccentric or off-set position of the lateralization member 20 where the distance between such cut-out portion 24 and a point on the outer circumference of the lateralization member 20 varies. In another exemplary embodiment where the lateralization member 20 can have a substantially circular cylindrical shape, the cut-out portion 24 can be positioned away from the center of the lateralization member 20. The varying radial distance between the cut-out portion 24 and the outer circumference of the lateralization member 20 can provide a variable lateralization effect as will be described below. It will be appreciated that various alternative embodiments of the location of the cut-out portion 24 and the form of the lateralization member 20 are still within the scope of the present invention.

In a further exemplary embodiment, the lateralization member 20 can comprise interference fittings 28 on the inner wall 26. In an exemplary embodiment, the interference fittings 28 can be formed to be complementary to the interference fittings 18 on the outer wall 16 of the supporting member 10. In one exemplary embodiment, the interference fittings 28 on the inner wall 26 can be engaged with the interference fittings 18 on the outer wall 16 to mount the lateralization member 20 on the supporting member 10. In another exemplary embodiment, the interference fittings 18 and 28 can assist to provide a variable lateralization effect as will be described below. It will be appreciated that various alternative embodiments of forming the lateralization member 20 are still within the scope of the present invention.

The lateralization member 20 can be supported by the supporting member 10 in various manners to form the lateralization device 1. In an exemplary embodiment such as shown in FIG. 1, the lateralization member 20 can be provided, which can at least partially surround the supporting member 10 and be supported thereby. In another exemplary embodiment, the cut-out portion 24 of the lateralization member 20 can be made to fit onto the post member 12 of the supporting member 10 to assemble the lateralization device 1. Various means can be used to retrain the relationship between the supporting member 10 and the lateralization member 20. In an exemplary embodiment, various conventional fasteners can be used to the position of the lateralization member 20 in relation to that of the supporting member 10.

In another exemplary embodiment, the supporting member 10 and the lateralization member 20 can be provided with complimentary engaging elements to restrain their relative movement to each other. For example, the inner wall 26 of the lateralization member 20 can be provided with interference fittings 28, which are complementary to the interference fittings 18 on the outer wall 16 of the supporting member 10. The complementary interference fittings 18 and 28 can allow the lateralization member 20 to join the supporting member 10 and be supported thereby.

Figure 4:
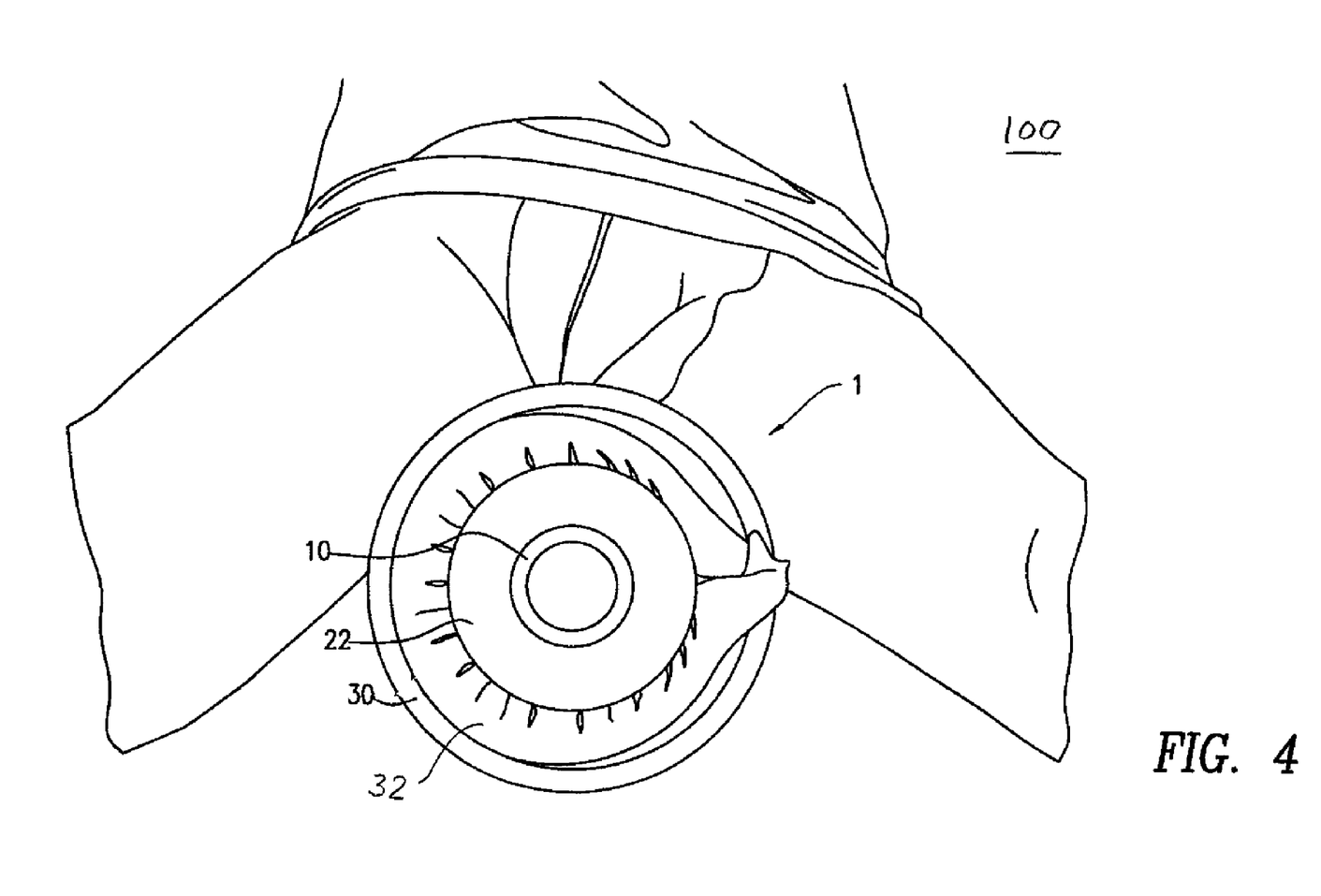
FIG. 4 illustrates an alternative embodiment of the lateralization device in its use position.
Figure 5:
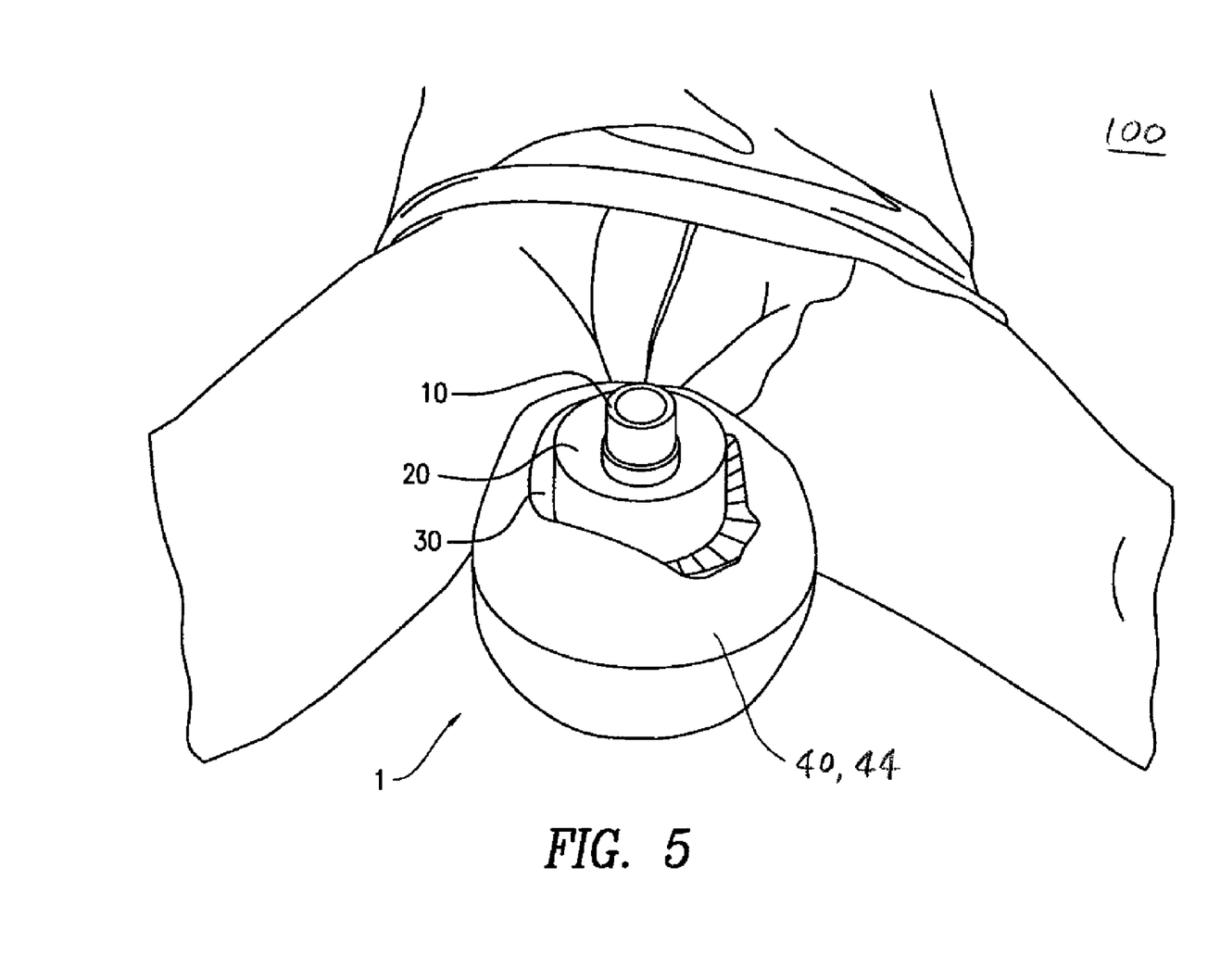
FIG. 5 illustrates the lateralization device of FIG. 4 with a protection member surrounding the lateralization member.
Figure 6:
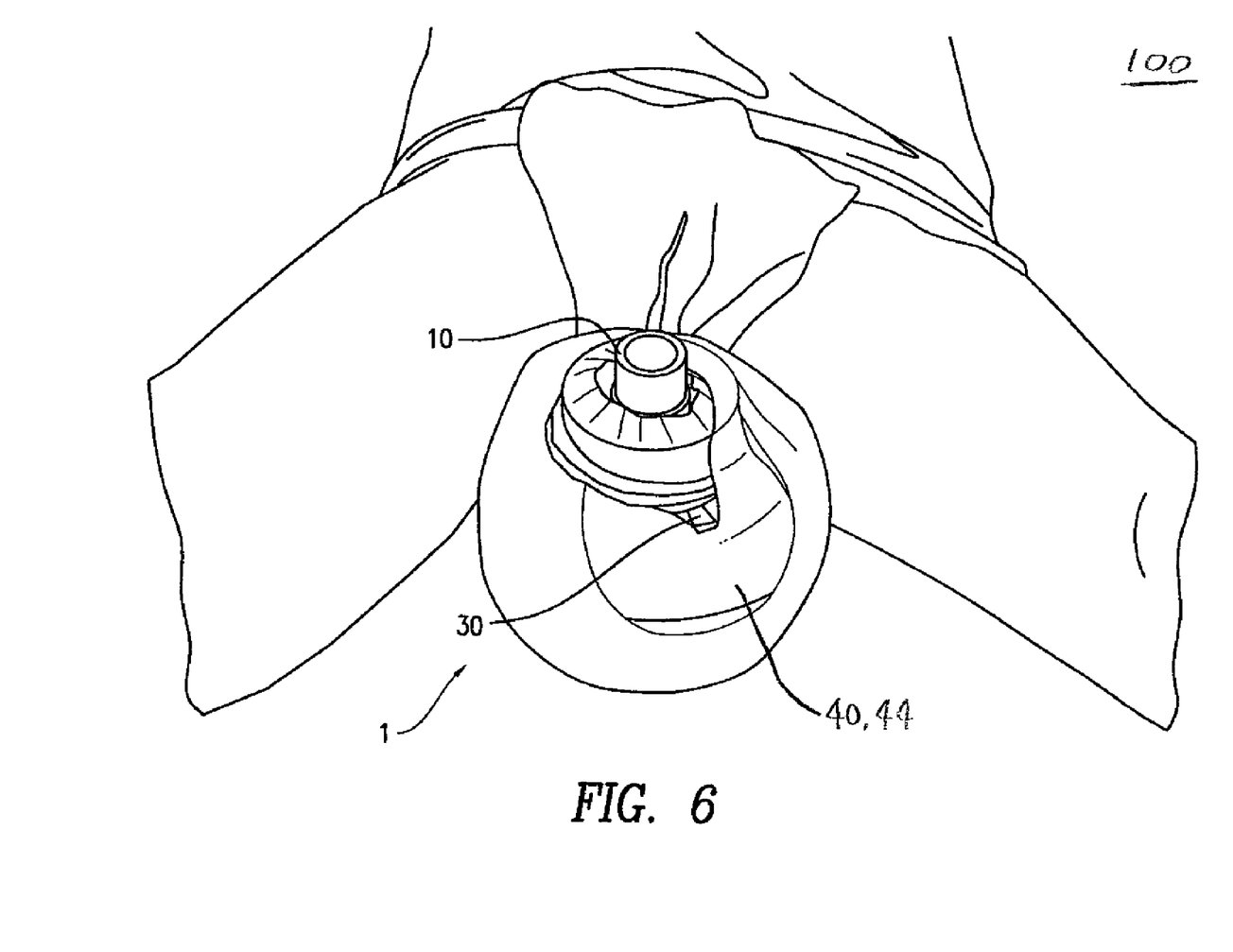
FIG. 6 illustrates the lateralization device of FIG. 4 with an alternative protection member surrounding the lateralization member.

In a further exemplary embodiment, such as shown in FIGS. 4 to 6, the lateralization member 20 can comprise a padding member 30. The padding member 30 can be so formed that, after being mounted onto such as the supporting member 10, the padding member 30 is capable of providing a lateral support for a user's body portion, such the user's femur. Additionally or alternatively, the padding member 30 can be formed that at least a portion thereof is capable of yielding to, without bottoming out, a pressure exerted thereon so as to provide a cushioning effect to the user's body portion. In one exemplary embodiment, the padding member 30 can be made of a yieldable material, such as a rubber like material. In another exemplary embodiment, the padding member 30 can be formed to be filed with a flowable or deformable material of any solid, liquid, gaseous, or gel state. In an exemplary embodiment, the padding member 30 can be a jelly pad 32. It will be appreciated that various alternative embodiments of forming the padding member 30 are still within the scope of the present invention.

In one exemplary embodiment, the padding member 30 can be adapted to at least partially wrap around the supporting member 10 and be mounted thereonto through various conventional means. For example, the padding member 30 can be directly mounted to the supporting member 10 by taping, bandaging, and the like. In an exemplary embodiment, the padding member 30 can completely wrap around the supporting member 10. In another exemplary embodiment, the padding member 30 can wrap around the supporting member 10 for more than one layer. In an exemplary embodiment where the padding member 30 is adapted to wrap around the supporting member 10 for one or more layers, the padding member 30 can be secured to itself by taping, bandaging, or other closure elements such as hook fasteners, Velcro fasteners, and the like. In a further embodiment, the padding member 30 can be used in combination with another lateralization member 20, such as a cylindrical member 22 mounted onto the supporting member 10. In an exemplary embodiment, the padding member 30 can be mounted onto either the supporting member 10, or the other lateralization member 20 or both in a similar manner. It will be appreciated that various alternative embodiments of mounting the padding member 30 are still within the scope of the present invention.

In another exemplary embodiment, a plurality of lateralization members 20 can be used to provide an adequate or desired lateralization effect. In one exemplary embodiment, such as shown in FIGS. 4 to 6, a first lateralization member 20 in the form of a cylindrical member 22 can be provided and mounted onto the supporting member 10. A second lateralization member 20, such as in the form of a padding member 30, can be provided to at least partially wrap around and mounted onto the cylindrical member 22. It will be appreciated that various alternative embodiments of forming the of forming the lateralization device 1 are still within the scope of the present invention.

Additionally or alternatively, the supporting member 10 and the lateralization member 20 can be assembled before the installation of the lateralization device 1. In one exemplary embodiment, the lateralization member 20 can be assembled to the supporting member 10 after the installation of the supporting member 10. For example, the supporting member 10 can be pre-installed on the fracture table. It will be appreciated that various alternative embodiments of assembling the supporting member 10 and the lateralization member 20 are still within the scope of the present invention.

In another embodiment, the lateralization device 1 is capable of providing a variable lateralization effect. For example, the lateralization device 1 can be formed and/or adjusted in various manners to provide a variable lateralization effect as desired. In an exemplary embodiment, the cylindrical member 22 of the lateralization member 20 can have an oval cross-section. The lateralization member 20 so formed is capable of a variable lateralization effect depending how the lateralization device 1 is oriented when being mounted on the support frame. For example, when the major diameter of the oval cylindrical member 22 is oriented in a lateral direction, the lateralization device 1 is capable of providing a maximum lateralization effect. On the other hand, a maximum lateralization effect can be obtained by orienting the minor diameter of the oval cylindrical member 22 in a lateral direction. It will be appreciated that variable lateralization effect can be achieved by orienting such an oval cylindrical member 22 in different directions.

In another exemplary embodiment, such as shown in FIG. 1, the supporting member 10 can be associated with the lateralization member 20 in an off-set relationship as described above. For example, the cut-out portion 24 can be formed in an off-set location in the lateralization member 20. After assembling the two members 10 and 20, the lateralization member 20 can be made to rotate around the supporting member 10 to provide a variable lateralization effect.

In a further exemplary embodiment, the lateralization member 20, which is in the form of a padding member 30, can be formed to provide a variable lateralization effect. In one exemplary embodiment, the size and number of the padding member 30 can be designed or selected to provide various degrees of lateralization effects. For example, a greater degree of lateralization effect is needed for an adult user, while a less degree of lateralization effect is more appropriate for a child user. In an exemplary embodiment, a series of the padding members 30 of various thicknesses can be provided and interchanged with one another to provide a variable lateralization effect. In another exemplary embodiment, such as shown in FIGS. 4 and 5, a plurality of padding members 30 can be combined to provide a greater degree of a lateralization effect. In a further exemplary embodiment, such as shown in FIGS. 4 and 5, one or more padding members 30 can be used in conjunction with a cylindrical member 22 to provide an adequate and/or variable lateralization effect.

In another exemplary embodiment, such as shown in FIGS. 4 and 5, a plurality of lateralization members 20 can be provided, which can be interchanged or combined to provide a desired and/or adequate lateralization effect. In an exemplary embodiment, the lateralization member 20 can be fixed to the supporting member 10 by various conventional means to secure the desired lateralization. In another exemplary embodiment, different types of the lateralization members 20 can be combined and used together to provide a variable lateralization effect. For example, lateralization members 20 in the form of a circular cylindrical member 22 and a padding member 30 can be joined together to afford a variable and comprehensive lateralization effect. It will be appreciated that the different combinations of the various lateralization members 20 can provide a variable lateralization effect.

In another exemplary embodiment, the lateralization member 20 can be adjusted or otherwise manipulated to provide a variable lateralization effect. For example, the lateralization member 20 can be oriented in various directions in relation to the supporting member 10 to provide a variable lateralization effect. In an exemplary embodiment, such as shown in FIG. 1, the inner wall 26 of the lateralization member 20 can be provided with interference fittings 28, which are complementary to the interference fittings 18 on the outer wall 16 of the supporting member 10. The complementary interference fittings 18 and 28 can allow the lateralization member 20 to rotate in relation to the supporting member 10 to provide a desired lateralization. Such desired lateralization can be secured during the medical procedure through one or more conventional fasteners (not shown) in various conventional manners. It will be appreciated that various alternative embodiments of providing a variable lateralization effect are still within the scope of the present invention.

If desired, a protection member 40 can be provided to at least partially wrap around and mounted onto the lateralization member 20 to afford a cushioning and/or protective effect to the user's body portion, such as the user's perineum. For example, the protection member 40 can wrap around at least a portion of the lateralization member 20. In an exemplary embodiment, such as shown in FIG. 1, the protection member 40 can be a sleeve-like member 42 surrounding the lateralization member 20. The protection member 40 can be inflatable or filled with various fluids, such as gel and the like, or otherwise formed to provide a cushioning and/or protective effect. In another exemplary embodiment, such as shown in FIGS. 5 and 6, the protection member 40 can be a bandage material 44 wrapping and covering the lateralization member 20 for protection.

In one exemplary embodiment, the protection member 40 can be readily removed from the lateralization member 20. In one exemplary embodiment, the protection member 40 can comprise a series protection member units (not shown) of different sizes, such as different thickness. Such different sized units of the protection member 40 can be interchangeable, such as to vary the cushioning and/or protective effect. In another exemplary embodiment, the bandage material 44 can be readily removed and exchanged after each use. It will be appreciated that various alternative embodiments of forming the protection member 40 are still within the scope of the present invention.

The lateralization device 1 can be used in various medical procedures to provide a lateralization effect. In an exemplary embodiment, the lateralization device 1 can be adapted to provide an adequate lateralization and/or cushioning effect for the patient's hip joint in a hip arthroscopy. For example, the lateralization device 1 can be used in conjunction with a fracture table to provide a hip lateralization in a hip arthroscopy. In one exemplary embodiment, the lateralization device 1 can be mounted onto a fracture table so that the lateralization member 20 can support a body portion of the user, such as the user's femur. In another exemplary embodiment, the lateralization device 1 can be mounted on the fracture table by inserting the extension portion 14 into a cavity structure in the fracture table. The lateralization device 1 can then be fixed to the fracture table in a conventional manner. It will be appreciated that various alternative embodiments of mounting the lateralization device 1 are still within the scope of the present invention.

After the lateralization device 1 is installed, the supporting member 10 and the lateralization member 20 can provide support and lateralization, such as for a user's body portion. In an exemplary embodiment, after the lateralization member 20 is assembled with the supporting member 10, the lateralization member 20 can provide a lateral support to the user's body portion. For example, the user can be positioned so that a body portion of the user lies against the lateralization member 20, which is capable of providing a lateral support to that body portion.

In one exemplary embodiment, the lateralization member 20 can be adapted to provide a lateral support for the patient's hip joint in a hip arthroscopy. For example, the user can be positioned so that the femur portion lies against the lateralization member 20, which is capable of providing a lateralization effect to the user's hip joint. In an exemplary embodiment, such as shown in FIGS. 4 to 6, the lateralization member 20 can be positioned to support the user near the crotch area during hip arthroscopy. It will be appreciated that other embodiments for using the lateralization device 1 are still within the scope of the present invention.

According to another aspect of the invention, a method is contemplated to provide a lateralization effect for a user's body portion. In one embodiment, the method can provide a desired lateralization and maintain the desired lateralization in various medical procedures. For example, in a hip arthroscopy, a lateralization effect can be provided so that the patient's hips can be forced laterally apart and further away from each other. It will be appreciated that the method can be applied to other body portions of a user to achieve a desired lateralization effect.

In another embodiment, the method is capable of providing a variable lateralization effect. In one exemplary embodiment, the method can comprise providing a first lateralization effect. The method can also comprise providing a second lateralization effect that differs from the first lateralization effect. In another exemplary embodiment, the method can comprise changing the lateralization till a desired lateralization effect is reached. For example, the lateralization can be changed between a minimum amount and a maximum amount. Additionally or alternatively, the lateralization can be changed gradually. In a further exemplary embodiment, the lateralization effect can be changed gradually to reach the desired amount. It will be appreciated that various alternative embodiments of providing the lateralization effect are still within the scope of the present invention.

Additionally or alternatively, the method can comprise maintaining a desired lateralization effect. Various means can be used to carry out the above method step. In an exemplary embodiment, the lateralization effect can be maintained by using a lateralization member capable of resisting a predetermined amount of force without yielding. In another exemplary embodiment, a lateralization device can be formed so that it requires an additional manipulation to vary the lateralization effect. Such a lateralization device is capable of maintaining a desired lateralization effect without the additional manipulation. It will be appreciated that various alternative embodiments of maintaining the lateralization effect are still within the scope of the present invention.

Optionally, the method can comprise providing a cushioning and/or protective effect, such as to the body portion of the user. In an exemplary embodiment, such cushioning and/or protective effect can be varied as desired.

It will be appreciated that the various features described herein may be used singly or in any combination thereof. Therefore, the present invention is not limited to only the embodiments specifically described herein. While the foregoing description and drawings represent a preferred embodiment of the present invention, it will be understood that various additions, modifications, and substitutions may be made therein without departing from the spirit and scope of the present invention. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. The presently disclosed embodiment is therefore to be considered in all respects as illustrative and not restrictive, the scope of the invention being not limited to the foregoing description.

What is claimed is:

1. A lateralization device for providing a lateralization effect to a body portion of a user, comprising:
    a supporting member comprising an outer wall and adapted to be supported in a fixed position, the supporting member further comprising a plurality of interference fittings on the outer wall; and
    a lateralization member mounted onto the supporting member and extending laterally therefrom to provide a lateralization effect to a user's body portion, the lateralization member comprising a recessed portion formed by an inner wall and comprising a plurality of interference fittings on the inner wall that are complementary to the interference fittings of the supporting member, the number of interference fittings on the inner wall being greater than the number of complementary interference fittings on the outer wall;
    wherein an angular orientation of the lateralization member against the supporting member is adjustable, and wherein mere adjustment of the angular orientation of the lateralization member against the supporting member is sufficient to alter the lateralization effect.

2. The lateralization device of claim 1, wherein the supporting member comprises a post member, and the post member comprises the outer wall.

3. The lateralization device of claim 1, wherein the lateralization member is formed of a material that can resist a pressure exerted thereon and maintain its initial shape during a normal use.

4. The lateralization device of claim 1, wherein the lateralization member comprises a substantially cylindrical member.

5. The lateralization device of claim 4, wherein the cylindrical member has a substantially circular cross-section.

6. The lateralization device of claim 5, wherein the recessed portion is located in an eccentric position on the cylindrical member.

7. The lateralization device of claim 1, wherein the lateralization member comprises a padding member.

8. The lateralization device of claim 7, wherein the padding member is an elongated member and adapted to wrap around the lateralization member for more than one time.

9. The lateralization device of claim 1, wherein the lateralization member can rotate in one direction in relation to the supporting member.

10. The lateralization device of claim 1 further comprising a protection member at least partially wrapped around the lateralization member.

11. The lateralization device of claim 1, wherein the supporting member is adapted to be mounted onto a fracture table.

12. The device of claim 1, wherein the lateralization member is expandable in a lateral direction.

13. A method for providing a lateralization effect to a user's body portions in a medical procedure, the method comprising:
    providing a lateralization vector force to part the user's body portions; and
    positioning the user's body portions throughout the medical procedure via a device according to claim 1 whereby an angular orientation of a lateralization member against a supporting member is adjustable to thereby alter said lateralization effect; wherein the lateralization vector force is exerted on the user's hip portion in a hip arthroscopy to provide a hip lateralization.

* * * * *